United States Patent
Sachdeva et al.

(10) Patent No.: US 6,688,885 B1
(45) Date of Patent: *Feb. 10, 2004

(54) METHOD AND APPARATUS FOR TREATING AN ORTHODONTIC PATIENT

(75) Inventors: Rohit Sachdeva, Plano, TX (US); Ron Jennings, Plano, TX (US); David M. Schaller, Dallas, TX (US); Thomas Weise, Berlin (DE); Rudger Rubbert, Berlin (DE); Friedrich Riemeier, Berlin (DE); Gary Sadow, Greer, SC (US)

(73) Assignee: OraMetrix, Inc, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/560,642

(22) Filed: Apr. 28, 2000

Related U.S. Application Data

(63) Continuation-in-part of application No. 09/451,560, filed on Nov. 30, 1999, now Pat. No. 6,540,512.

(51) Int. Cl.[7] ................................................ A61C 3/00
(52) U.S. Cl. ........................................................ 433/24
(58) Field of Search ................................. 433/2, 3, 24

(56) References Cited

U.S. PATENT DOCUMENTS

| | | | |
|---|---|---|---|
| 4,575,805 A | 3/1986 | Moermann et al. | |
| 5,011,405 A | 4/1991 | Lemchen | |

(List continued on next page.)

FOREIGN PATENT DOCUMENTS

| | | |
|---|---|---|
| DE | 44 45 552 | 6/1995 |
| DE | 196 36 354 | 3/1998 |

(List continued on next page.)

OTHER PUBLICATIONS

Syrinx, Bending Robot, Syrinx Technologies, Inc Richardson TX (no date).

Syrinx, Orthotherm, Syrinx Technologiesm Inc Richardson TX (no date).

(List continued on next page.)

*Primary Examiner*—Ralph A. Lewis
(74) *Attorney, Agent, or Firm*—McDonnell Boehnen Hulbert & Berghoff

(57) ABSTRACT

A method and apparatus for treating an orthodontic patient include processing that begins by generating digital information regarding the orthodontic patient by a site orthodontic system. The site orthodontic system then transmits the digital information to an orthodontic server, which creates an electronic patient record therefrom. The orthodontic server then generates an initial treatment from the electronic patient record, wherein the initial treatment plan includes precise steps to obtain a desired orthodontic structure. The orthodontic server then transmits a digital version of the initial treatment plan to the site orthodontic system. Upon confirmation from the site orthodontic system, the orthodontic server designs an orthodontic apparatus for one of the precise steps based on the treatment plan. The orthodontic apparatus is then fabricated and provided to the site orthodontic system. At predetermined points in time after installation of the orthodontic apparatus in accordance with the treatment plan, the patient's mouth is electronically scanned to obtain updated digital information. The site orthodontic system provides the updated digital information to the orthodontic server, which uses the updated digital information to update the electronic patient record. From the updated electronic patient record, the orthodontic server determines whether the actual movement of the patient's teeth is as predicted. If so, the next step of the initial treatment plan is executed. If, however, the actual movement is not as predicted, the orthodontic server adjusts the treatment plan to obtain the desired results. After the treatment plan has been adjusted, the next step of the revised treatment plan is executed. This monitoring of a patient's progress and revising the treatment plan, when necessary, continues throughout the treatment.

20 Claims, 11 Drawing Sheets

U.S. PATENT DOCUMENTS

| | | |
|---|---|---|
| 5,238,404 A | 8/1993 | Andreiko |
| 5,338,198 A | 8/1994 | Wu et al. .................... 433/213 |
| 5,368,478 A | 11/1994 | Andreiko et al. |
| 5,395,238 A | 3/1995 | Andreiko et al. |
| 5,431,562 A | 7/1995 | Andreiko et al. |
| 5,447,432 A | 9/1995 | Andreiko et al. |
| 5,454,717 A | 10/1995 | Andreiko et al. |
| 5,456,600 A | 10/1995 | Andreiko et al. |
| 5,464,349 A | 11/1995 | Andreiko et al. |
| 5,474,448 A | 12/1995 | Andreiko et al. |
| 5,518,397 A | 5/1996 | Andreiko et al. |
| 5,533,895 A | 7/1996 | Andreiko et al. |
| 5,542,842 A | 8/1996 | Andreiko et al. |
| 5,618,176 A | 4/1997 | Andreiko et al. |
| 5,683,243 A * | 11/1997 | Andreiko et al. ............... 433/3 |
| 5,772,585 A * | 6/1998 | Lavin et al. ................. 600/300 |
| 5,879,158 A | 3/1999 | Doyle et al. ................... 433/24 |
| 5,975,893 A | 11/1999 | Chishti et al. ................. 433/6 |
| 6,068,482 A | 5/2000 | Snow ........................ 433/223 |
| 6,099,314 A | 8/2000 | Kopelman et al. .......... 433/213 |
| 6,217,325 B1 | 4/2001 | Chishti et al. ................ 433/24 |
| 6,227,850 B1 | 5/2001 | Chishti et al. ................ 433/24 |
| 6,227,851 B1 | 5/2001 | Chishti et al. ................ 433/24 |
| 6,315,553 B1 | 11/2001 | Sachdeva et al. ............. 433/24 |
| 6,464,496 B1 * | 10/2002 | Sachdeva et al. ............. 433/24 |
| 2002/0025503 A1 | 2/2002 | Chapoulaud et al. ......... 433/24 |
| 2002/0028417 A1 | 3/2002 | Chapoulaud et al. ......... 433/24 |

FOREIGN PATENT DOCUMENTS

| | | |
|---|---|---|
| DE | 196 38 727 | 3/1998 |
| DE | 196 38 758 | 3/1998 |

OTHER PUBLICATIONS

Syrinx, 3D Scanner, Syrinx Technologies, Inc. Richardson TX (no date).

Co–pending U.S. patent application of Rohit Sachdeva et al. Ser. No. 09/451,560 filed Nov. 30, 1999.

Co–pending U.S. patent application of Rohit Sachdeva et al., Ser. No. 09/560,646 filed Apr. 28, 2000.

S.M. Yamany and A.A. Farag, "A System for Human Jaw Modeling Using Intra–Oral Images" *Proc. IEEE Eng. Med. Biol. Soc. (EMBS) Conf.*, vol. 20, Hong Kong, Oct. 1998, pp. 563–566.

S.M. Yamany, A.A. Farag, David Tasman, A.G. Farman, "A 3–D Reconstruction System for the Human Jaw Using a Sequence of Optical Images," *IEEE Transactions on Medical Imaging*, vol. 19, No. 5, May 2000, pp. 538–547.

* cited by examiner

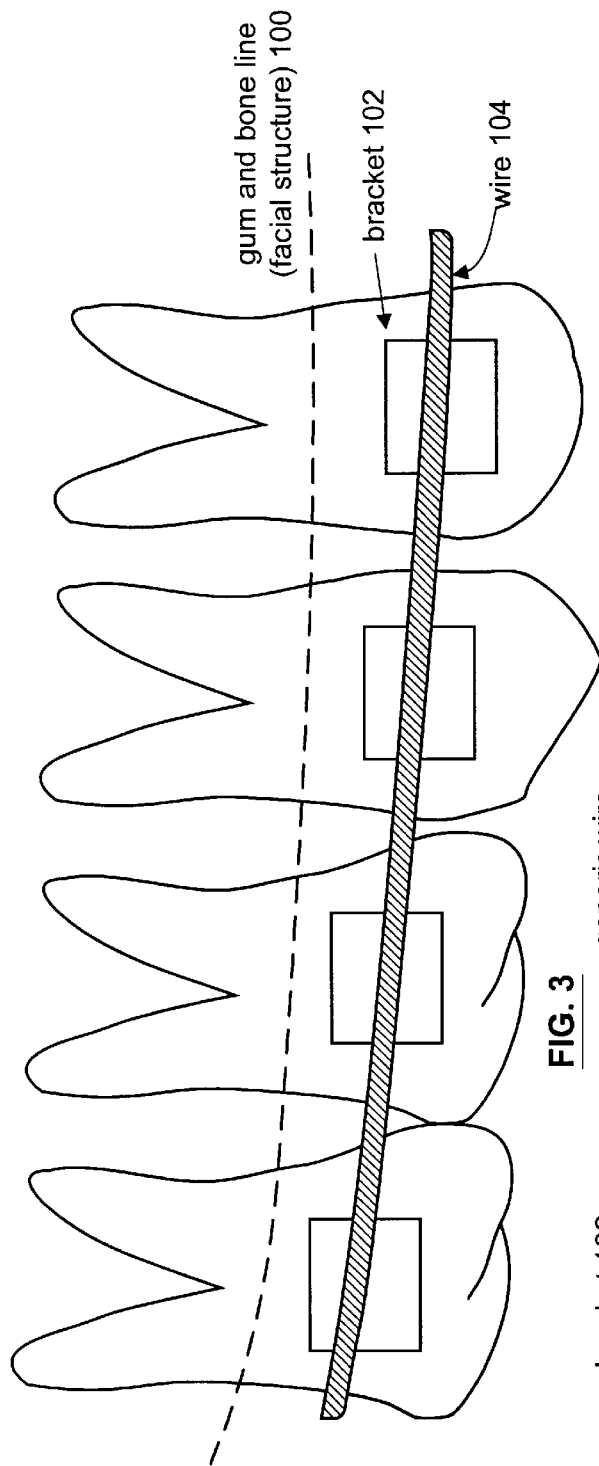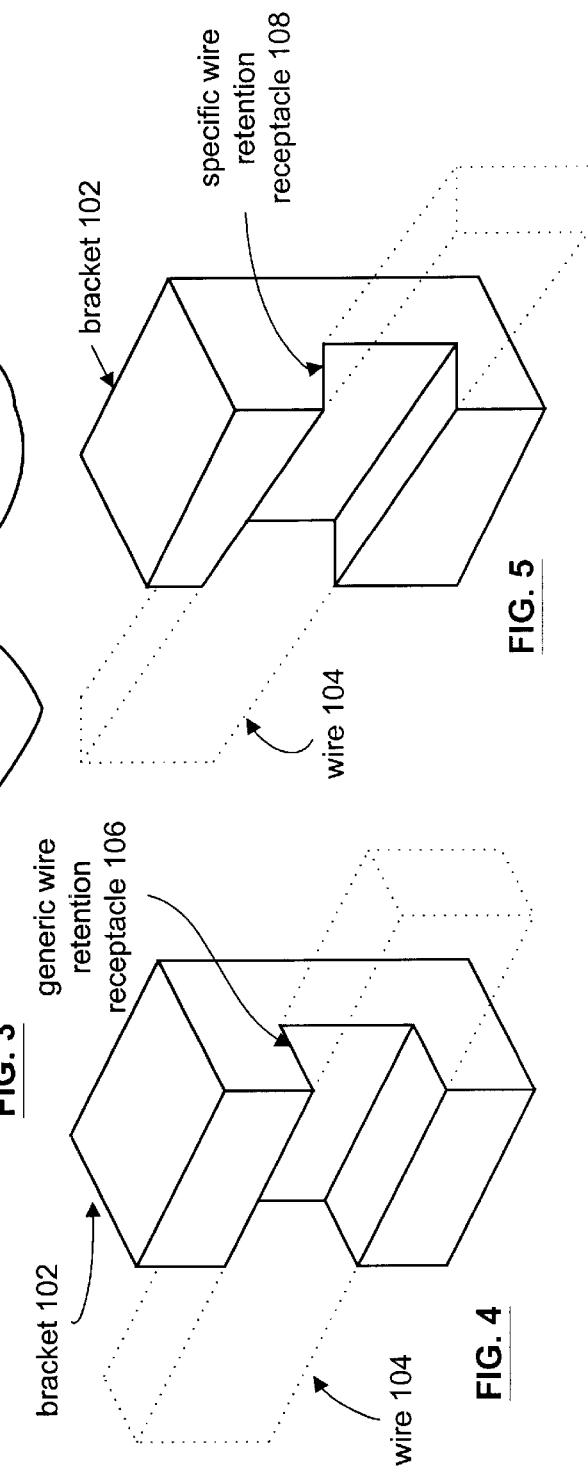

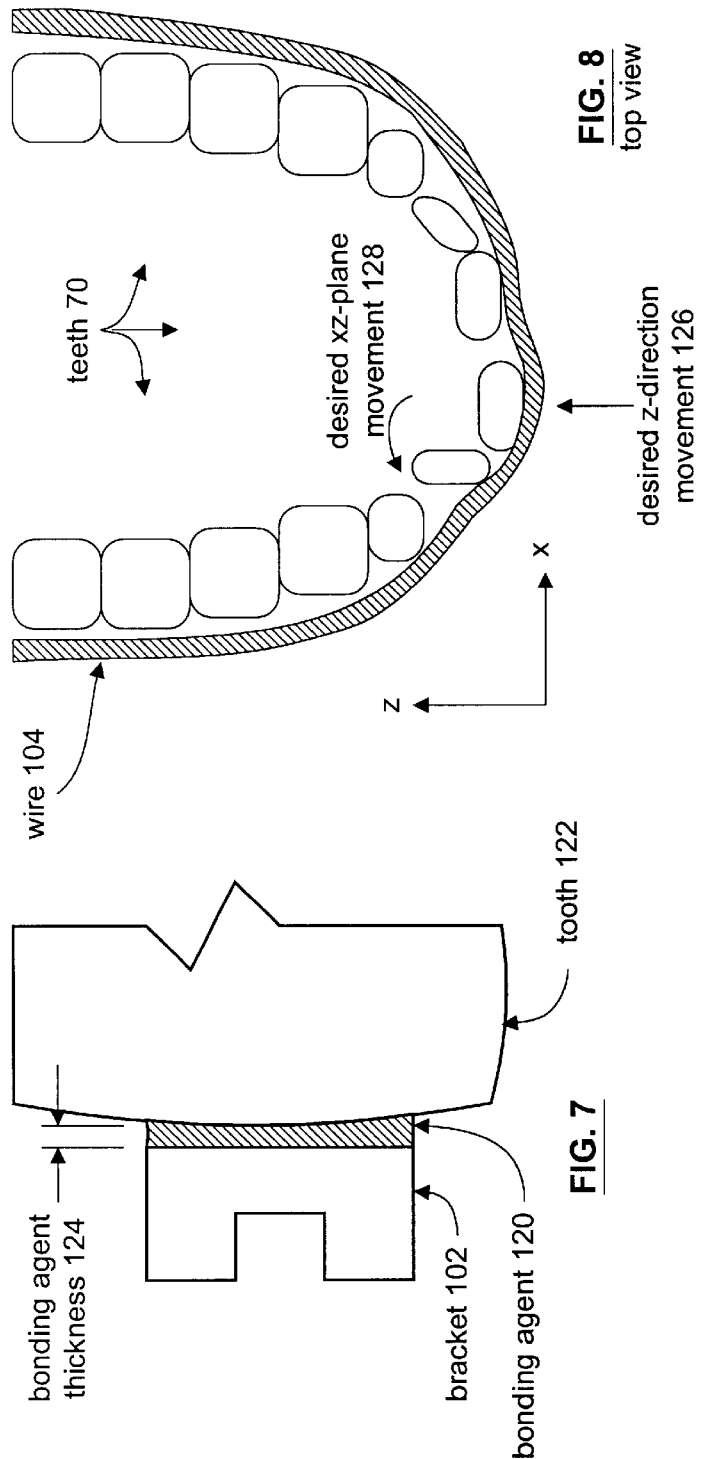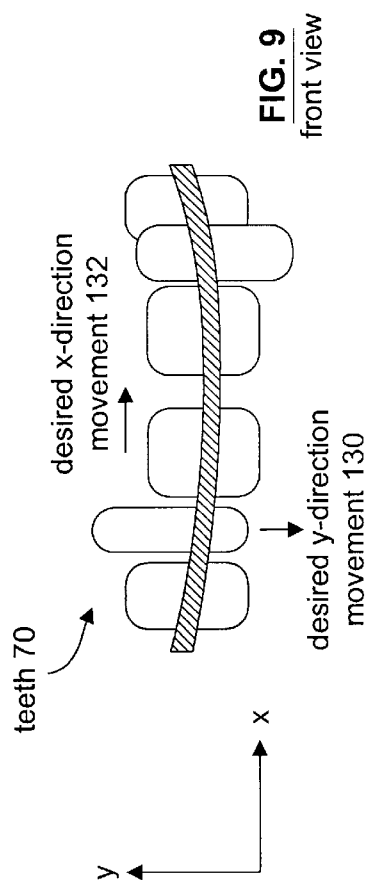

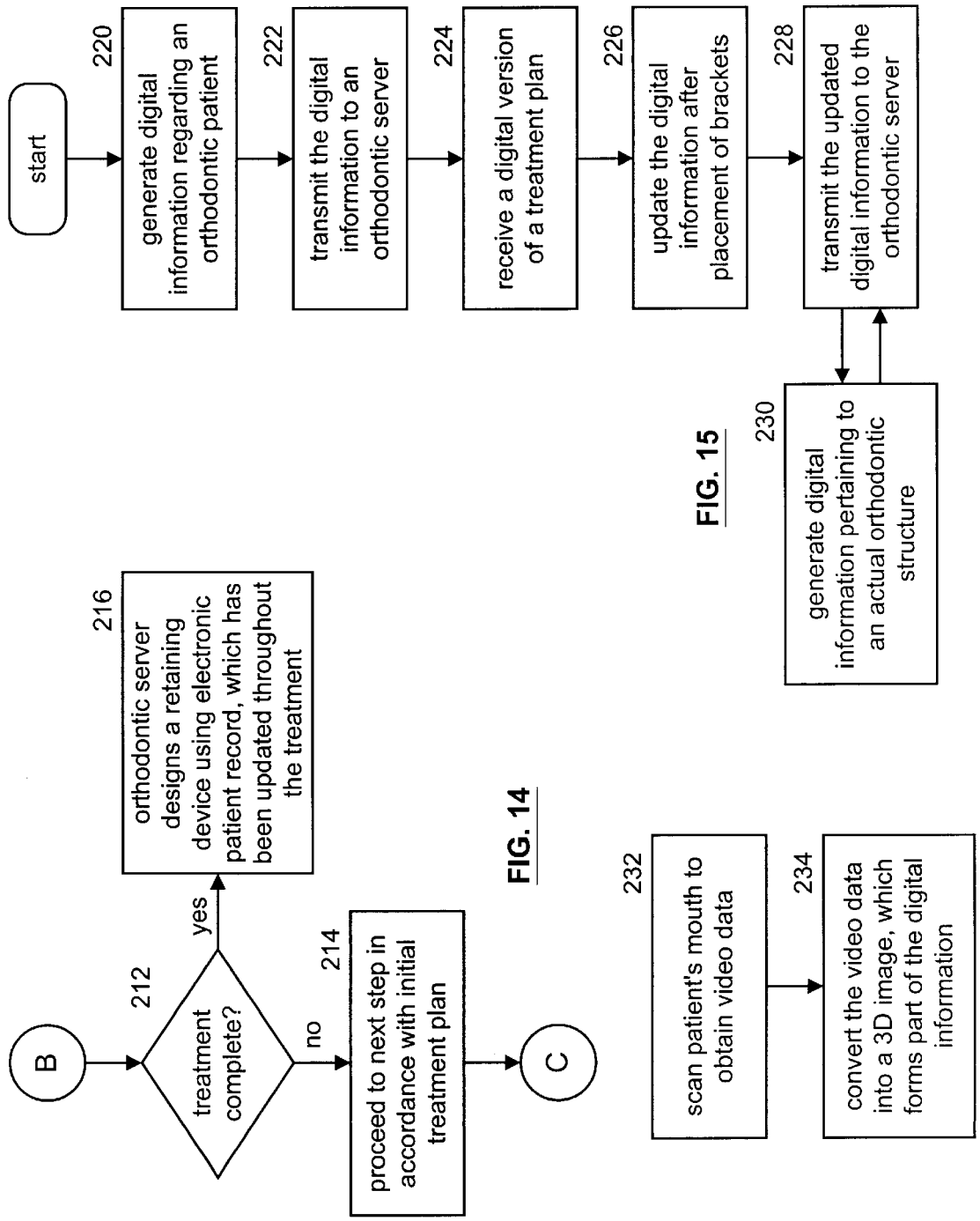

METHOD AND APPARATUS FOR TREATING AN ORTHODONTIC PATIENT

CROSS REFERENCE TO RELATED APPLICATION

This is a continuation-in-part of Ser. No. 09/451,560, filed Nov. 30, 1999, now U.S. Pat. No. 6,540,512.

TECHNICAL FIELD OF THE INVENTION

This invention relates generally to the practice of orthodontics and in particular to a method and apparatus for treating an orthodontic patient.

BACKGROUND OF THE INVENTION

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Unfortunately, the current innovations to change the practice of orthodontic from an art to a science have only made limited progress. This limit is due in part by the brackets being the focal point for orthodontic manipulation. By having the brackets as the focal point, placement of each bracket on a corresponding tooth is critical. Since each bracket includes a custom sized and positioned wire retaining groove, a misplacement of a bracket by a small amount (e.g., an error vector having a magnitude of millimeter or less and an angle of a few degrees or less) can cause a different force system (i.e., magnitude of movement and direction of movement) than the desired force system to be applied to the tooth. As such, the tooth will not be repositioned to the desired location.

Another issue with the brackets being the focal point is that once the brackets are placed on the teeth, they are generally fixed for the entire treatment. As such, if the treatment is not progressing as originally calculated, the orthodontist uses his or her expertise to make the appropriate changes. The treatment may not progress as originally calculated for several reasons. For example, misplacement of a bracket, misapplication of a bend in the wire, loss or attrition of a bracket, bonding failure, the patient falls outside of the "normal" patient model (e.g., poor growth, anatomical constraints, etc.), patient lack of cooperation in use of auxiliary appliance, etc. are factors in delayed treatment results. When one of these conditions arise, the orthodontist utilizes his or her expertise to apply manual bends to the wire to "correct" the errors in treatment. Thus, after the original scientific design of the brackets, the practice of the orthodontic converts back to an art for many patients for the remainder of the treatment.

Another issue with the brackets being the focal point is that customized brackets are expensive. A customized bracket is produced by milling a piece of metal (e.g., stainless steel, aluminum, ceramic, titanium, etc.) and tumble polishing the milled bracket. While the milling process is very accurate, some of the accuracy is lost by tumble polishing. Further accuracy is lost in that the placement of the brackets on the teeth and installation of the wire are imprecise operations. As is known, a slight misplacement of one bracket changes the force on multiple teeth and hinders treatment. To assist in the placement of the custom brackets, they are usually shipped to the orthodontist in an installation jig. Such an installation jig is also expensive. Thus, such scientific orthodontic treatment is expensive and has many inherent inaccuracies.

Therefore, a need exists for a method and apparatus that provides a scientific approach to orthodontic care throughout the treatment, minimizes the treatment cycle, decreases patient inconvenience and discomfort, and maintains treatment costs.

BRIEF DESCRIPTION OF THE DRAWINGS

FIG. 3 illustrates a graphical representation of an orthodontic apparatus being applied to a patient's teeth in accordance with the present invention;

FIG. 4 illustrates an isometric view of a bracket having a generic wire retention receptacle in accordance with the present invention;

FIG. 5 illustrates an isometric view of a bracket including a specific wire retention receptacle in accordance with the present invention;

FIG. 7 illustrates a graphical representation of a bracket bonded to a tooth in accordance with the present invention;

FIG. 8 illustrates a top view of a patient's mouth wherein the wire provides movement in an XZ plane in accordance with the present invention;

FIG. 9 illustrates a graphical diagram of the wire providing movement of the teeth in the X and Y direction in accordance with the present invention;

FIGS. 12 through 14 illustrate a logic diagram of a method for treating an orthodontic patient in accordance with the present invention;

FIG. 15 illustrates a logic diagram of a method for monitoring a patient's progress in accordance with the present invention.

DETAILED DESCRIPTION OF A PREFERRED EMBODIMENT

Figure 1:
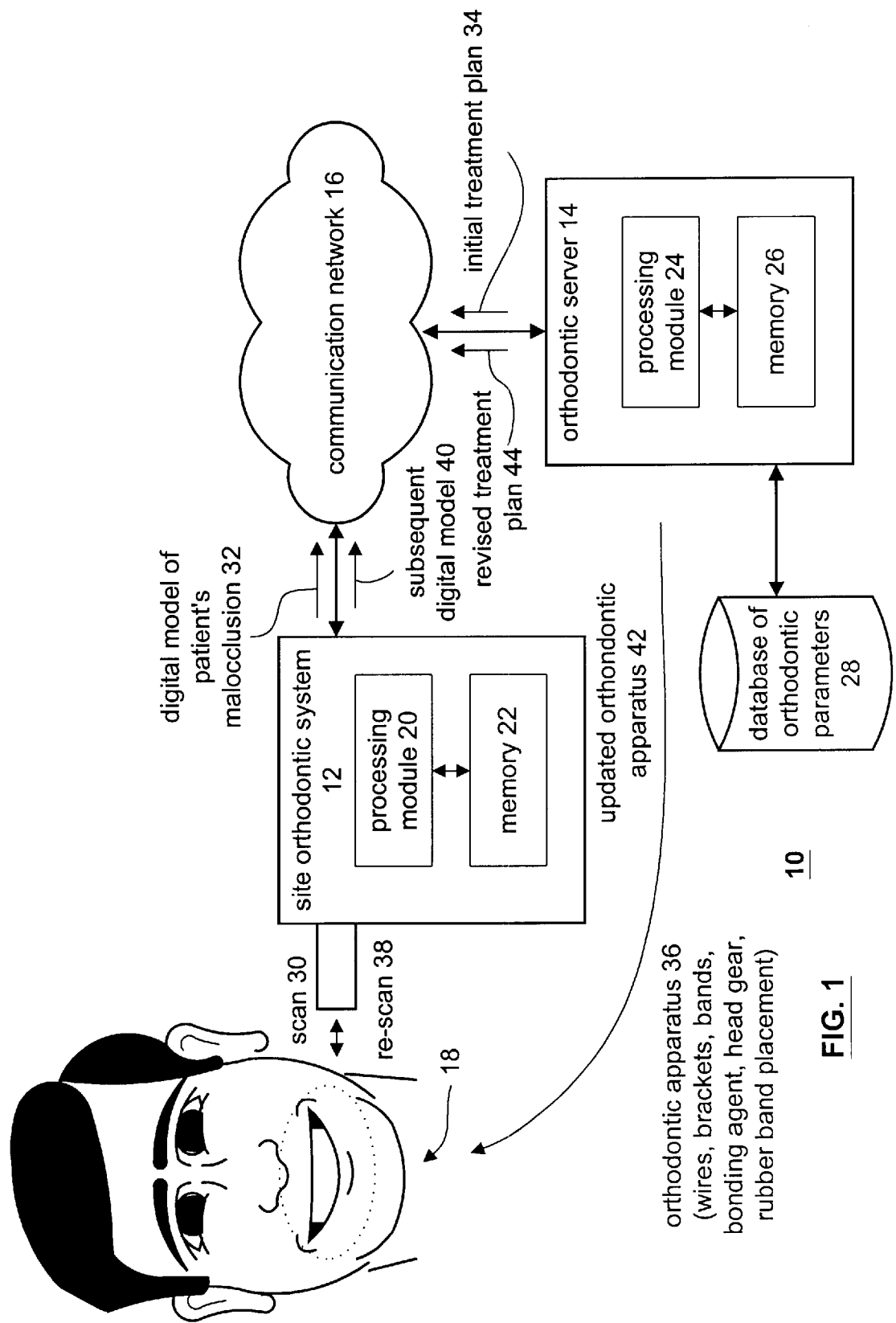
FIG. 1 illustrates a schematic block diagram of an orthodontic system in accordance with the present system.

Generally, the present invention provides a method and apparatus for treating an orthodontic patient. Such method and apparatus include processing that begins by generating digital information regarding the orthodontic patient by a site orthodontic system. The digital information may include a three-dimensional scan image of the patient's orthodontic structure (e.g., teeth, jaw bone, gums, and other facial features), x-rays, clinical examination and measurements, dental history, medical history, photographs, etc. The site orthodontic system then transmits the digital information to an orthodontic server. The orthodontic server and/or the site orthodontic system creates an electronic patient record from the digital information. The electronic patient record includes, but is not limited to, clinical examination interpretations, radiology examination measurements, automatic and manual cephalometric analysis, a created electronic cephalometric tracings, an electronic composite including an integration of the three-dimensional images, radiographic data (e.g., x-rays, CAT scans, MRI scans), photographs, a generated electronic articulation module, measurements and analysis of electronic models, data quality assurance checks, and/or supplemental data.

The orthodontic server then generates an initial treatment plan from the electronic patient record, wherein the initial treatment plan includes precise steps to obtain a desired orthodontic structure. In other words, the initial treatment plan includes a series of steps, wherein, for each step, a corresponding orthodontic apparatus will be designed to reshape the patient's orthodontic structure into a desired structure for the precise step. The orthodontic server then transmits a digital version of the initial treatment plan to the site orthodontic system. Upon confirmation from the site orthodontic system, the orthodontic server designs an orthodontic apparatus (e.g., brackets, bands, wires, head gear, rubber band placement, and/or a retainer) for one of the precise steps based on the treatment plan. The orthodontic apparatus is then fabricated/assembled and provided to the site orthodontic system. In addition, the orthodontic server may provide practitioner and/or patient instructions for use, maintenance, and/or installation of the orthodontic apparatus.

Upon receipt of the orthodontic apparatus, the orthodontist verifies receipt of the orthodontic apparatus and subsequently installs it. At predetermined point in time after the installation in accordance with the treatment plan, the patient's mouth is electronically scanned to obtain updated digital information. The site orthodontic system provides the updated digital information to the orthodontic server, which uses the updated digital information to update the electronic patient record. From the updated electronic patient record, the orthodontic server determines whether the actual movement of the patient's teeth is as predicted. Such a determination may be supplemented with input from a practitioner (e.g., a technician, dental assistant, orthodontist, specialist, consultant, etc.) at the site or at a remote site with respect to the patient. If so, the next step of the initial treatment plan is executed (e.g., the wire for the next step is fabricated, provided to the orthodontist, and installed). If, however, the actual movement is not as predicted, the orthodontic server adjusts the treatment plan to obtain the desired results. After the treatment plan has been adjusted, the next step of the revised treatment plan is executed. This monitoring of a patient's progress and revising the treatment plan, when necessary, continues throughout the treatment. Thus, with such a method and apparatus, a scientific approach is provided to orthodontic treatment throughout the treatment, maintains the treatment costs at reasonable levels, and provides a more consistent and reduced treatment time. In addition, the present method and apparatus allow orthodontic practitioners to have just-in-time inventory, allows for treatment adjustments that would be required due to changes in tooth position and/or jaw development, and further allows for changes in the orthodontic structure if the force system becomes sub-optimal.

The present invention can be more fully described with reference to FIGS. 1 through 16. FIG. 1 illustrates an orthodontic system 10 that includes a site orthodontic system 12 and an orthodontic server 14 that are operably coupled together via a communication network 16. The site orthodontic system 12 includes a scanner (not shown) to scan the mouth and facial features of a patient 18. The site orthodontic system 12 also includes a processing module 20 and memory 22. The processing module 20 may be a single processing device or a plurality of processing devices. Such a processing device may be a microprocessor, microcomputer, digital signal processor, central processing unit of a computer or work station, digital circuitry, state machine, and/or any device that manipulates signals (e.g., analog and/or digital) based on operational instructions. The memory 22 may be a single memory device or a plurality of memory devices. Such a memory device may be a random access memory, read-only memory, floppy disk memory, hard drive memory, extended memory, magnetic tape memory, zip drive memory and/or any device that stores digital information. Note that when the processing module 20 implements one or more of its functions, via a state machine or logic circuitry, the memory storing the corresponding operational instructions is embedded within the circuitry comprising the state machine or logic circuitry.

The orthodontic server 14 includes a processing module 24 and memory 26. The processing module 24 may be a single processing device or a plurality of processing devices. Such a processing device may be a microprocessor, microcontroller, digital signal processor, microcomputer, central processing unit of a personal computer or a work station, logic circuitry, state machine and/or any other device that manipulates signals (analog and/or digital) based on operational instructions. The memory 26 may be a single memory device or a plurality of memory devices. Such a memory device may be read-only memory, random access memory, floppy disk memory, magnetic tape memory, hard drive memory, magnetic tape memory, and/or any device that stores digital information. Note that when the processing module 24 implements one or more of its functions, via a state machine or logic circuitry, the memory storing the corresponding operational instructions is imbedded within the circuitry comprising the state machine or logic circuitry.

The orthodontic server 14 is operably coupled to a database 28 of orthodontic parameters. The orthodontic parameters include, but are not limited to, age, gender, race, physical geometry of a patient's teeth, mouth structure, bone structure, type of malocclusion, ethnicity, function, etc. In general, the orthodontic parameters include any human characteristic related to orthodontics that affects tooth positioning, movement, function, stability, appearance, structure of the bones, teeth, gums, pathology, patient's knowledge, medical history, dental history, etc. and mechanical characteristics of the orthodontic apparatus that may be stored in a database system to enhance prediction of a patient's orthodontic treatment. In other words, the orthodontic parameters include case histories of previously treated patients that are used to determine normal expected treatments, mechanical aspects of the brackets, bands, and wire, mean deviation from normalized treatments, and other statistical information regarding the normalized treatment of an orthodontic patient. In addition, as the electronic patient records are received for new patients, and as the treatment for such patients is updated, this information is added to the database 28.

The communication network 16 coupling the site orthodontic system 12 to the orthodontic server 14 may be a local area network, wide area network, the Internet, the public switching telephone network (PSTN), a direct connect wire, ATM network, and/or any other type of data transport structure. Accordingly, the orthodontic system 10 may be a self-contained system when the communication network 16 is a direct connect wire. Such a self-contained system would reside at an orthodontist's office or treatment center (e.g., a center run by practitioners). Alternatively, the orthodontic system 10 may include a plurality of site orthodontic systems 12 located in the same building, or office, such that an orthodontist, or group of orthodontists, may have multiple treatment rooms for simultaneous patient treatment. As a further alternative, the orthodontic system 10 may include a plurality of site orthodontic systems 12 that are located in different geographic locations (e.g., different buildings, different offices, different towns, different states, or different countries) than the orthodontic server 14. In such a distributed system, the communication network 16 would be a wide area network, local area network, the Internet, and/or the PSTN. Still further, a distributed system may include a plurality of orthodontic servers 14.

Regardless of the configuration of the orthodontic system 10, the overall processing of a patient's orthodontic treatment is essentially the same. When it has been determined that a patient 18 is to receive orthodontic treatment, which may occur after several consultations with an orthodontist (several orthodontists, specialists, or dentists), the patient's orthodontic structure is scanned 30. The patient's orthodontic structure includes the patient's teeth, facial tissue, gums, bone structure, and any other physical feature that affects the patient's orthodontic treatment or is influenced by orthodontic care. The scanned image of the patient's orthodontic structure is provided to the site orthodontic system 12. Note that a specific embodiment of scanning is described in U.S. patent application Ser. No. 09/560,584 filed Apr. 28, 2000, and is hereby incorporated herein by reference. In addition, as an alternative to scanning the patient directly, a model, impression, or a stereolithograph (SLA) model may be scanned at the orthodontic site or the site of the server. Further note that the patient information may be referenced by a code to provide anonymity to the identity of the patient.

The site orthodontic system 12 converts the scanned image of the patient's orthodontic structure into a digital model of the patient's malocclusions 32. Such a conversion is done by receiving the scanned image of the patient's orthodontic structure, x-rays of the patient's orthodontic structure, photographs, and/or other patient information and generating the three-dimensional (3-D) digital model therefrom. Such a conversion process is described in co-pending patent application having a title of "Method and Apparatus for Producing a Three-Dimensional Digital Model of an Orthodontic Patient", Ser. No. 09/560,641 filed Apr. 28, 2000 which is hereby incorporated herein by reference. Alternatively, the site orthodontic system 12 may pass the scanned data, the x-rays, and the other patient information to the orthodontic server 14 and the orthodontic server 14 generates the 3-D digital model.

The site orthodontic system 12 then transports the digital model of the patient's malocclusions 32 and an electronic patient record via the communication network 16 to the orthodontic server 14. The electronic patient record is a compilation of patient specific information that is beneficial in treating the patient and includes, but is not limited to, clinical examination interpretations, radiology examination measurements, automatic and manual cephalometric analysis, a created electronic cephalometric tracings, an electronic composite including an integration of the three-dimensional images, radiographic data (e.g., x-rays, CAT scans, MRI scans), photographs, a generated electronic articulation module, measurements and analysis of electronic models, data quality assurance checks, patient's demographic data, patient's chief complaint, disclaimer forms, insurance, medical history, dental history, patient's progress notes, patient's billing schedule and tracking, patient educational information, and/or supplemental data. Based on this information, and/or practitioner inputs, orthodontic parameters of like cases are retrieved from the database 28, which is used by the orthodontic server 14 to generate an initial treatment plan 34. The orthodontic treatment plan includes a plurality of precise steps applied in sequence to obtain a desired orthodontic structure. Generation of the initial treatment plan is described in co-pending patent applicant entitled "Method and Apparatus for Automated Generation of a Patient Treatment Plan", Ser. No. 09/560,647 filed Apr. 28, 2000, which is hereby incorporated herein by reference.

The orthodontic server 14 provides the initial treatment plan to the site orthodontic system 12 via the communication network 16. If the site orthodontic system 12 confirms the initial treatment plan 34 (e.g., the orthodontist provides inputs to the system 12 that the patient and orthodontist agree to the treatment plan), the orthodontic server 14 designs an orthodontic apparatus 36. The designing of the orthodontic apparatus is described in co-pending patent application entitled "Method and Apparatus for Designing an Orthodontic Apparatus to Provide Tooth Movement", Ser. No. 09/560,128 filed Apr. 28, 2000, which is hereby incorporated herein by reference. The orthodontic apparatus 36 includes at least a wire, and/or a wire and brackets, and may further include one or more of bands, bonding agent thickness, headgear, rubber bands, bracket placement provide information, a retaining device, functional appliances (e.g., Herbst appliance, expander, etc.) and other mechanical devices to provide tooth movement (active apparatus) and/or tooth anchoring (passive apparatus). The orthodontic apparatus 36 is then fabricated/assembled and provided to the orthodontists for installation on the patient 18.

After the orthodontic apparatus 36 has been installed in the patient for a given period of time (e.g., two to six weeks as prescribed in the treatment plan), the patient's orthodontic structure is rescanned 38. The rescanned orthodontic structure is converted into a digital model of the patient's current stage of malocclusion 32 by the site orthodontic system 12. The site orthodontic system 12 then provides the revised, or a new, digital model of the patient's current stage of malocclusion 32 to the orthodontic server 14. The orthodontic server 14 determines whether the actual orthodontic structure of the patient corresponds to the calculated or estimated orthodontic structure per the corresponding step of the initial treatment plan. The estimated orthodontic structure is determined based on the initial treatment plan and the corresponding design of the apparatus structure. If the actual orthodontic structure (e.g., the current positioning of the teeth) substantially match the estimated orthodontic structure, the orthodontic server 14 causes the next orthodontic apparatus 36 to be generated in accordance with the next step of the initial treatment plan. For the purposes of this discussion, a substantial match occurs when the three-dimensional position of the teeth in the actual orthodontic structure are less than one millimeter different in any one of the X, Y and Z direction than the estimated placement (i.e., the calculated position for the corresponding step of the initial treatment plan), when the function of the upper and lower arches are substantially as predicted, stability of the teeth is substantially as desired, and/or the appearance is substantially as desired for the given step. Note that the orthodontic structure may be scanned immediately after placement of the brackets to verify correct bracket placement, such verification will be discussed in greater detail with reference to FIG. 13.

If the orthodontic server 14 determines that the actual orthodontic structure does not match the estimated orthodontic structure, the orthodontic server 14 adjusts the treatment plan based on the actual orthodontic structure, related orthodontic parameters used to create the initial treatment plan, inputs from a practitioner, any other orthodontic parameters to accommodate the revised treatment plan, and the desired orthodontic structure. Based on the revised treatment plan, the orthodontic server 14 designs the next orthodontic apparatus 36 to be applied. The newly designed orthodontic apparatus 36 is provided to the orthodontist for installation on the patient. This process continues for each installation of the orthodontic apparatus 36 on the patient's mouth until the treatment plan has been completed. Typically, the orthodontic apparatus 36 will include, for the initial orthodontic apparatus installation, bracket and a wire having bends to provide a three-dimensional displacement or stabilization of at least one tooth. For subsequent steps of the treatment plan, the orthodontic apparatus includes a wire and may further include rubber band placement, head-gear, etc. As such, a closed loop system is provided to treat an orthodontic condition of a patient in a scientific manner throughout the treatment. By utilizing wires to provide the three-dimensional displacement of teeth, corrections throughout the treatment plan may readily be made to achieve the desired orthodontic structure. In addition, customized wires provide more rapid treatment due to optimal forces being applied to each tooth. As one of average skill in the art will appreciate, the orthodontic apparatus will be fabricated to provide the appropriate tooth displacement in accordance with the treatment plan. As such, a wire may provide one-dimensional tooth displacement, two-dimensional tooth displacement, three-dimensional tooth displacement or tooth stabilization in any one of the three planes of space.

Alternative uses of the orthodontic system 10 include, but are not limited to, a one time use that generates all the wires needed for treatment, use to assist in bracket placement, generate a single super elastic wire and one finishing wire, and/or a one time use for comparative diagnostic. As one of average skill in the art will appreciate, the orthodontic system 10 may be used in a variety of ways to make the practice of orthodontic more of a science than an art. In addition, various levels of security may be used within the system 10, allowing certain users access to all information while restricting access of others to a portion of the information.

Figure 2:
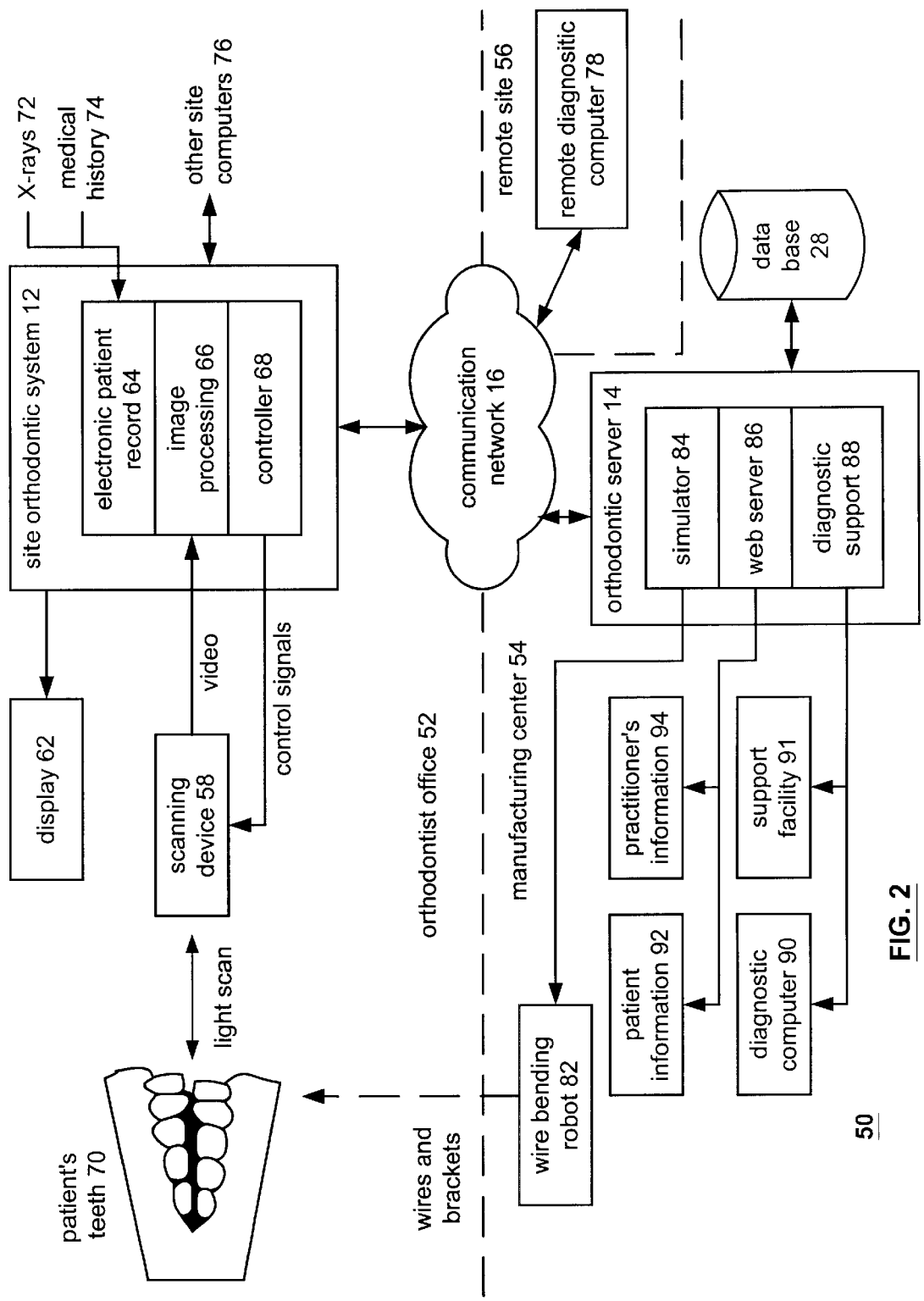
FIG. 2 illustrates an alternate schematic block diagram of an orthodontic system in accordance with the present invention.

FIG. 2 illustrates a schematic block diagram of an alternate orthodontic system 50. The orthodontic system 50 includes at least two sites, an orthodontist's office, or orthodontic treatment facility, 52 and a manufacturing center 54 (e.g., a laboratory). The system 50 may also include a remote site 56. The portion of the system 50 located at the orthodontists office 52 includes site orthodontic system 12, a display 62, and a scanning device 58. The orthodontic' office 52 may also include other site computers 76 that integrate the orthodontist's office computers into a single system. As such billings, records, inventory, etc. may be networked together within the site orthodontic system 50 to provide a single system at the orthodontist's office 52. In addition, the system 50 may be networked with product manufacturers of the orthodontic apparatus materials.

The scanning device 58 provides a white light signal, laser, ultra sound, and/or infrared on to the patient's teeth 70 to obtain a scanned image. Such scanning is done under the control of the site orthodontic system 60 via control signals. The scanning device 58 retrieves a static or dynamic image of the patient's teeth, which is provided to the site orthodontic system 12.

The site orthodontic system 12 includes an electronic patient section 64, an image processing section 66, a controller section 68, and a user interface section (not shown). Note that each of these separate sections may be achieved via operational instructions stored in memory 22 and executed by the processing module 20. The electronic patient section 64 contains the three-dimensional scanned images of the patient, x-rays, clinical exams and measurements, dental history, medical history, patient consent forms, photographs, template entries such as chief complaints, etc., free form entries, and extra data. The image processing module 66 receives the data of the patient's teeth and produces therefrom the three-dimensional image. The digital information is provided to the orthodontic server 14 via the communication network 16. Note that controller 68 provides control signals to the scanning device 58 which cause the scanning device 58 to obtain the video information, or scanned image, of the patient's teeth 70. Such video information includes, but is not limited to, live video images, still video images, and/or photographs.

The orthodontic server 14, the database 28 and a wire bending robot 82 are located at the manufacturing center 54. The orthodontic server 14, upon receiving the information from the site orthodontic system 12 generates an electronic patient record for this particular patient. The electronic patient record includes, but is not limited to, clinical examination and interpretations, radiological examination measurements, automatic and manual cephalometric analysis, created electronic cephalometric tracings, an electronic composite of the 3-D images, radio graphic data, and photographs, generated electronic articulation models, measured and analyzed electronic modules, data quality assurance checks and/or supplemental data.

The orthodontic server 14 includes a simulator module 84, a web server 86, and a diagnostic support module 88. The simulator module 84 utilizes the electronic patient record and orthodontic parameters from the database 28 to design the orthodontic apparatus. The design of the wire is then provided to the wire bending robot 82, which bends the wire of the orthodontic apparatus in three-dimensions such that the wire provides three-dimensional displacement of the patient's teeth. If the orthodontic apparatus includes auxiliary appliances, the design for such appliances is provided to a manufacturer for fabrication. By having the wire provide the three-dimensional displacements, the brackets applied to the patient's teeth may be generic. As such, the orthodontic apparatus of the present invention is considerably less expensive than the customized brackets of previous orthodontic treatments, improves the accuracy of orthodontic care, and reduces the criticalness of bracket placement. The wire bending robot 82 may be a bending robot as manufactured by OraMetrix, Inc.

The web server 86 provides a web page for patients to obtain patient information 92 and for practitioners to access practitioner information 94. As such, the orthodontic server 14 may provide patients with a web page for answers to frequently asked questions, chat groups, tips on maintaining proper dental care during orthodontic treatment and/or any information related to a patient's dental and/or orthodontic care needs. The orthodontic server 14 may also provide practitioner information 94 to practitioners. Such information 94 may be located on a web page that provides practitioners with information related to the practice of orthodontic. In addition, the web page may provide information related to the particular patient being treated. Such information may be accessed utilizing a password or some form of encryption key.

The orthodontic server 14 includes a diagnostic support module 88 that actually generates the corresponding information that is provided to the simulator 84. The diagnostic support module 88 may be coupled to a diagnostic computer 90 and support facility equipment 91. The diagnostic computer 90 may be operated by an orthodontist or professional associated with the manufacturing center 54 to coordinate the design and maintenance of the orthodontic apparatus. In addition, the diagnostic computer provides an input for practitioners to provide the clinical examination information and other patient related data. The support facility 91 may include a personal computer, or work station, that tracks patient billing information, and/or supplemental patient information relating to the orthodontic treatment.

The system 50 may also include a remote diagnostic computer 78 located at the remote site 56. The remote diagnostic computer 78 allows orthodontists and/or other practitioners not located at the manufacturing center 54 to provide input as to the orthodontic treatment of a particular patient. In addition, the remote diagnostic computer 78 may be operated by a specialist who has been consulted for a particular case.

The initial treatment plan generated by the orthodontic server 14 may include inputs from multi-faceted disciplines. For example, before the orthodontic treatment can begin a physician may need to be consulted for particular medical reasons. For instance, a patient may require particular medications before each treatment to avoid complications of certain medical conditions. In addition, before orthodontic treatment can begin, tooth extraction may be required, thus consultation with a dentist is needed. Further, a patient may require special treatment such as jaw surgery, headgear, rubber bands, etc. If special treatment is needed, the database 28 is accessed to determine whether there is a case match. If so, the case history for the previous treatment is integrated into the treatment plan for the present patient. If a case match was not found, the orthodontic practitioner's at the manufacturing site 54 using their expertise, the expertise of the care provider, consultants, etc., and/or near match case histories, to generate the initial treatment plan.

The wire-bending robot 82 generates the wires having three-dimensional bends to provide three-dimensional displacement of the patient's teeth. Based on inputs of the orthodontic server, the wire-bending robot generates the corresponding wires for each step of the treatment plan. Note that a full series of wires may be generated at one time, or the wires can be generated one at a time in accordance with a corresponding step of the treatment plan. By utilizing the wire bending robot 82 precise bends, loops, and/or other force system manipulations in the wires may be obtained thereby eliminating the inaccuracies of human wire bending. In addition, three-dimensional bends may be achieved to provide three-dimensional displacement, or stabilization, of one or more teeth. As such, the displacement of teeth is primarily incorporated into the wires such that generic brackets may be used on the patient's teeth thereby reducing the costs. In addition, by utilizing the close loop system as shown in FIG. 2, subsequent wires in the treatment plan may be manipulated to give updated tooth displacement such that the desired orthodontic structure is obtained within the prescribed treatment time.

FIG. 3 illustrates a graphical representation of a patient's teeth having an orthodontic apparatus attached thereto. The orthodontic apparatus includes a plurality of brackets 102 and a wire 104. As shown, the brackets 102 and wire 104 are installed below the gum and bone line 100. Throughout the treatment, the brackets are fixed to the teeth whereby the wire 104 is manipulated to achieve the desired orthodontic structure (i.e., the desired tooth placement). The brackets 102 may be the type of brackets found in FIG. 4 or FIG. 5.

FIG. 4 illustrates a standard bracket or a generic prescription bracket 102 that includes a generic wire retention receptacle 106. For the standard bracket, the generic wire retention receptacle 106 is a simple groove (i.e., a slot) in the bracket 104 without complex angles or depths. For the generic prescription bracket 102, the generic wire retention receptacle 106 is a groove in the bracket 104 that includes a generic angularity. The wire 104 is inserted into the bracket as shown to provide the desired torque on the corresponding tooth.

FIG. 5 illustrates a custom bracket 102 having a specific wire retention receptacle 108. In this embodiment, the bracket has the retention receptacle 108 designed to include complex angles of depth and groove that are determined for a particular patient. As such, the orthodontic apparatus applied to a patient's teeth may include brackets having generic wires retention receptacles 106 or brackets having specific wire retention receptacles 108.

Figure 6:
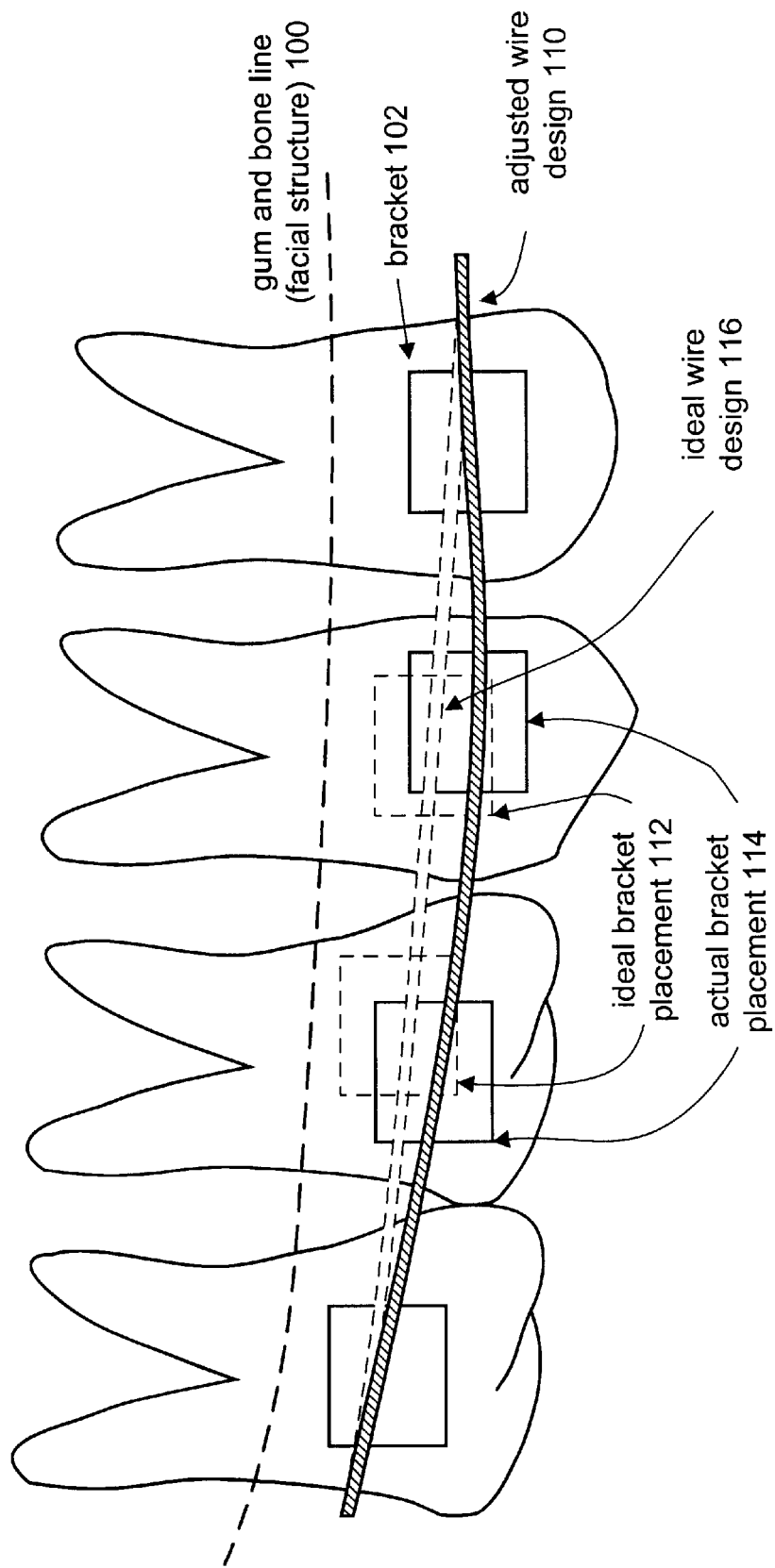
FIG. 6 illustrates a graphical representation of recalculating bends of a wire due to misplacement of brackets in accordance with the present invention.

FIG. 6 illustrates a graphical representation of the actual placement of brackets and wire on the patient's teeth. The actual bracket placement 102 is shown by the solid lines while the ideal bracket placement 112 is shown by the dashed lines. Correspondingly the adjusted wire design 110 is shown in solid lines while the ideal wire design 116 is shown in dashed lines. As previously mentioned, with current technologies that utilize the bracket to provide the force system for tooth displacement, the location of the bracket on the tooth is critical. As such, a bracket misplacement in prior art implementations causes non optimal tooth movement. With the present invention, the initial treatment plan may be created from the digital model of the patient's teeth prior to the installation of the brackets. The treatment plan may then be revised once the brackets are installed. As such, in the example shown in FIG. 6, when the actual bracket placement is not in the ideal bracket placement 112 location, the treatment plan may be adjusted thereby yielding the adjusted wire design 110. As such, even though the brackets are not in the initial ideal place, the treatment will still be ideal by redesigning the subsequent wires and/or a template, and/or instructions, on adjusting a present wire, to provide the desired displacement.

Note that, as the teeth move, the relative bracket position changes thereby causing the force system on the tooth to be different. In addition, each tooth surface is different, which, when a bracket is applied in accordance with a generic placement prescription, will generate a different force system causing varying tooth movement. The present invention allows for such conditions and compensates for such conditions utilizing the closed loop feedback system previously discussed. In addition, it is not uncommon for a patient to lose a bracket. When this occurs, the orthodontist is required to replace the bracket, which may not be replaced in the ideal location either due to misalignment by the practitioner or drift of the bracket. As such, once a bracket has been replaced, a new scan may be performed to obtain a new digital model such that corrected wire design may be performed.

FIG. 7 illustrates a tooth 122 having a bracket 102 bonded thereto. The bracket is bonded using a bonding agent 120, which has a thickness 124. Based on the thickness 124 of the bonding agent 120, the force system on the tooth may vary. As such, the present invention can incorporate the bonding agent thickness 124 into the treatment plan and compensate for variations thereof. In addition, the present invention may prescribe a particular bonding agent thickness 124 of varying angles and depths to achieve the desired tooth displacement. Still further, the base of the bracket may be angular in two or three-dimensions of space to provide further displacement options.

FIGS. 8 and 9 illustrate the three-dimensional displacement achieved by the wires fabricated in accordance with the present invention. In FIG. 8, which depicts a top view of a patient's teeth, the treatment plan indicates that one tooth is to have a Z direction movement 126 while a second tooth has a desired X, Z plane movement 128. The wire 104 is fabricated to provide the desired X, Z plane movement 128 and the desired Z direction movement 126. In addition, as shown in FIG. 9, the wire is fabricated to provide the desired X direction movement 132 of the first tooth and a desired Y direction movement 130 of the second tooth. As such, by fabricating the wire in accordance to the present invention, three-dimensional placement of the teeth 70 may be obtained.

Figure 10:
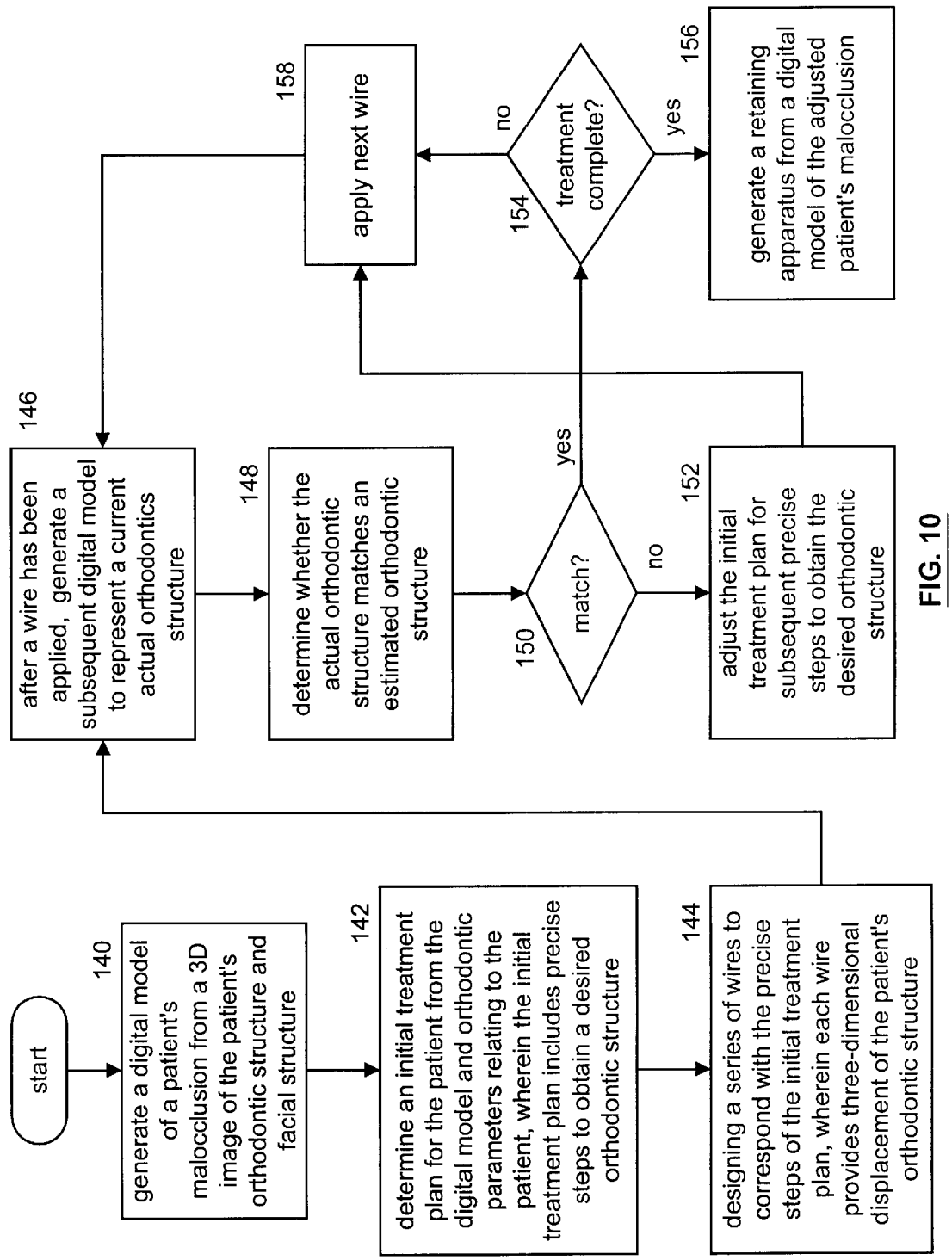
FIG. 10 illustrates a logic diagram of a method for designing a series of wires in accordance with the present invention.

FIG. 10 illustrates a logic diagram of a method performed by the orthodontic server 14 to assist in the treatment of an orthodontic patient. The process begins at step 140 where a digital model of a patient's malocclusion is generated from a three-dimensional image of the patient's orthodontic structure and/or facial structure. The three-dimensional image may be generated by scanning the patient's mouth and facial area. The orthodontic structure includes the patient's teeth, gums, jawbone, and associated soft tissue while the facial structure includes further facial bones and soft tissue. The process then proceeds to step 142 where an initial treatment plan is derived for the patient from the digital model and orthodontic parameters relating to the patient. The initial treatment plan includes precise steps to obtain a desired orthodontic structure. The process then proceeds to step 144 where a series of wires are designed to correspond with the precise steps of the initial treatment plan. Each wire is designed to provide three-dimensional displacement of the patient's orthodontic structure, when three-dimensional displacement is needed. In addition to designing the wires, the brackets may be fabricated for each tooth wherein each bracket includes a generic wire retention receptacle, a specific bonding thickness, a specific bracket base, and/or a specific wire retention receptacle.

Having fabricated the brackets, a wire is fabricated to provide three-dimensional displacement of the patient's orthodontic structure in accordance with a particular precise step. As such, for each step of the treatment plan, or revised treatment plan, a wire is fabricated to provide three-dimensional displacement for brackets including a generic wire retention receptacle. Alternatively, at least one of the brackets may be fabricated with a specific wire retention receptacle that assists in providing three-dimensional displacement of the patient's tooth in accordance with the particular precise step. In addition, the bracket bonding thickness, or base, may be determined to further provide three-dimensional displacement of the patient's orthodontic structure (i.e., the patient's tooth or teeth). Further, band sizing and fitting may be simulated as part of the orthodontic apparatus, which allows for electronic selection of an appropriate band size or fabrication.

The process then proceeds to step 146 where after a wire has been applied, a subsequent digital model is generated to represent a current actual orthodontic structure. The process then proceeds to step 148 where a determination is made as to whether the actual orthodontic structure substantially matches an estimated orthodontic structure. The process then proceeds to step 150 where the process branches depending on whether the determination at step 148 was a match. If the actual orthodontic structure did not match the estimated orthodontic structure (i.e., the calculated desired movement of the teeth), the process proceeds to step 152. At step 152, the initial treatment plan is adjusted for subsequent precise steps to obtain the desired orthodontic structure. As such, a three-dimensional configuration of a new corresponding orthodontic apparatus (e.g., the wire) for one of the subsequent precise steps is redefined. The process then proceeds to step 158 where the next wire is applied. Note that an adjustment to the treatment plan may simply be extended time to achieve the desired placement for a current step without changing a wire. Further note, that the next step may use the same wire, but add new bends to it. Still further note that the database of orthodontic parameters is updated with the digital models of abnormal treatment results of the patient to further enhance subsequent treatment. The process then reverts to step 146.

If, at step 150 a match occurred, the process proceeds to step 154. At step 154 a determination is made as to whether the treatment is complete. If not, the process proceeds to step 158 following the corresponding path. If, however, the treatment is complete the process proceeds to step 156 where a retaining apparatus is generated from a digital model of the adjusted patient's malocclusions.

Figure 11:
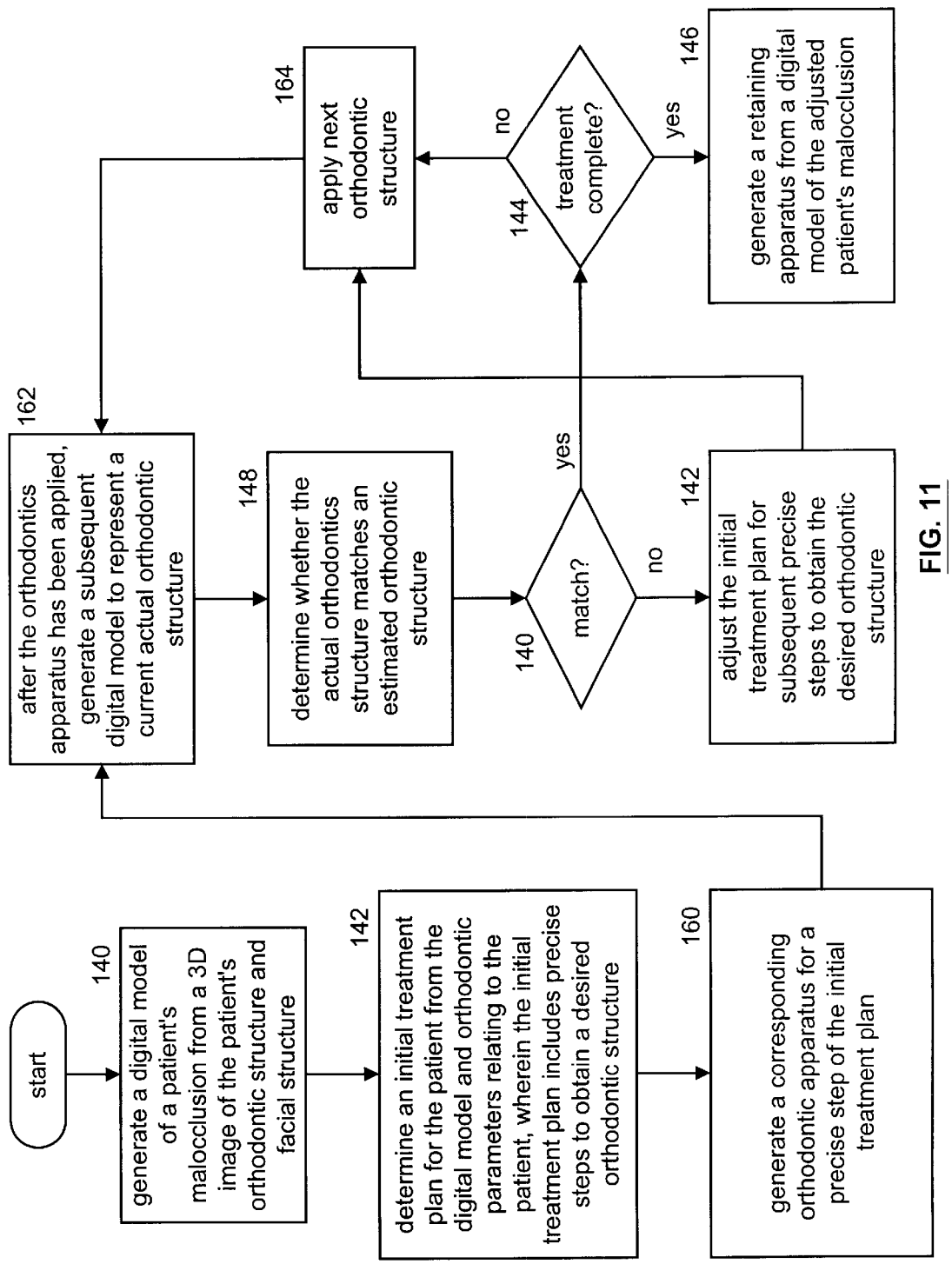
FIG. 11 illustrates a logic diagram of a method for designing an orthodontic apparatus in accordance with the present invention.

FIG. 11 illustrates a logic diagram of an alternate method for the orthodontic server to assist in the treatment of an orthodontic patient. The process begins at step 140 where a digital model of a patient's malocclusion is generated from a three-dimensional image of the patient's orthodontic structure and facial structure. This may be achieved by scanning the patient's oral cavity to obtain the digital model using a three-dimensional light scanner. The process then proceeds to step 142 where an initial treatment plan is determined for the patient from the digital model and orthodontic parameters relating to the patient. The initial treatment plan includes precise steps to obtain a desired orthodontic structure. The orthodontic parameters include, but are not limited to, age, gender, race, bone density, facial structure, tooth displacement, etc. Note that the digital model of the patient may be obtained subsequent to placement of the brackets on the patient's teeth. Having done this, the initial treatment plan may be adjusted to compensate for any manual misplacement of a bracket. Alternatively, the initial treatment plan may not be generated until after the initial placement of the brackets on the patient's teeth.

The process then proceeds to step 160 where a corresponding orthodontic apparatus is generated for a precise step of the initial treatment plan. The corresponding orthodontic apparatus may include a wire, bracket, headgear, rubber bands, and/or a retainer. The orthodontic apparatus may include a series of wires that correspond to the precise steps, a template for producing a wire for a given precise step, and/or an adjustment template for a wire of a subsequent precise step. If a template is developed, the orthodontist may make on-site accurate wire bend adjustments.

The process then proceeds to step 162 where a subsequent digital model is generated after the orthodontic apparatus has been applied to obtain a digital image of the actual orthodontic structure. Note that a new digital model is obtained and recorded each time a precise step of the initial treatment plan is performed. Similarly, if the treatment plan is altered, digital models are obtained for the revised orthodontic structure.

The process then proceeds to step 148 where a determination is made as to whether the actual orthodontic structure matches an estimated orthodontic structure. The process then proceeds to step 140 which routes further processing based on whether a match occurs. If a match does not occur, the process proceeds to step 142 where the initial treatment plan is adjusted for subsequent precise steps of the treatment plan to obtain the desired orthodontic structure. The process then proceeds to step 164 where the next orthodontic structure is applied to the patient's teeth. Having done this, the process repeats at step 162.

If the actual orthodontic structure substantially matches the estimated orthodontic structure, the process proceeds to step 144. At step 144, a determination is made as to whether the treatment is complete. If not, the process proceeds to step 164. If the treatment is complete, the process proceeds to step 146. At step 146, a retaining apparatus is generated from a digital model of the adjusted patient's malocclusion.

Figure 12:
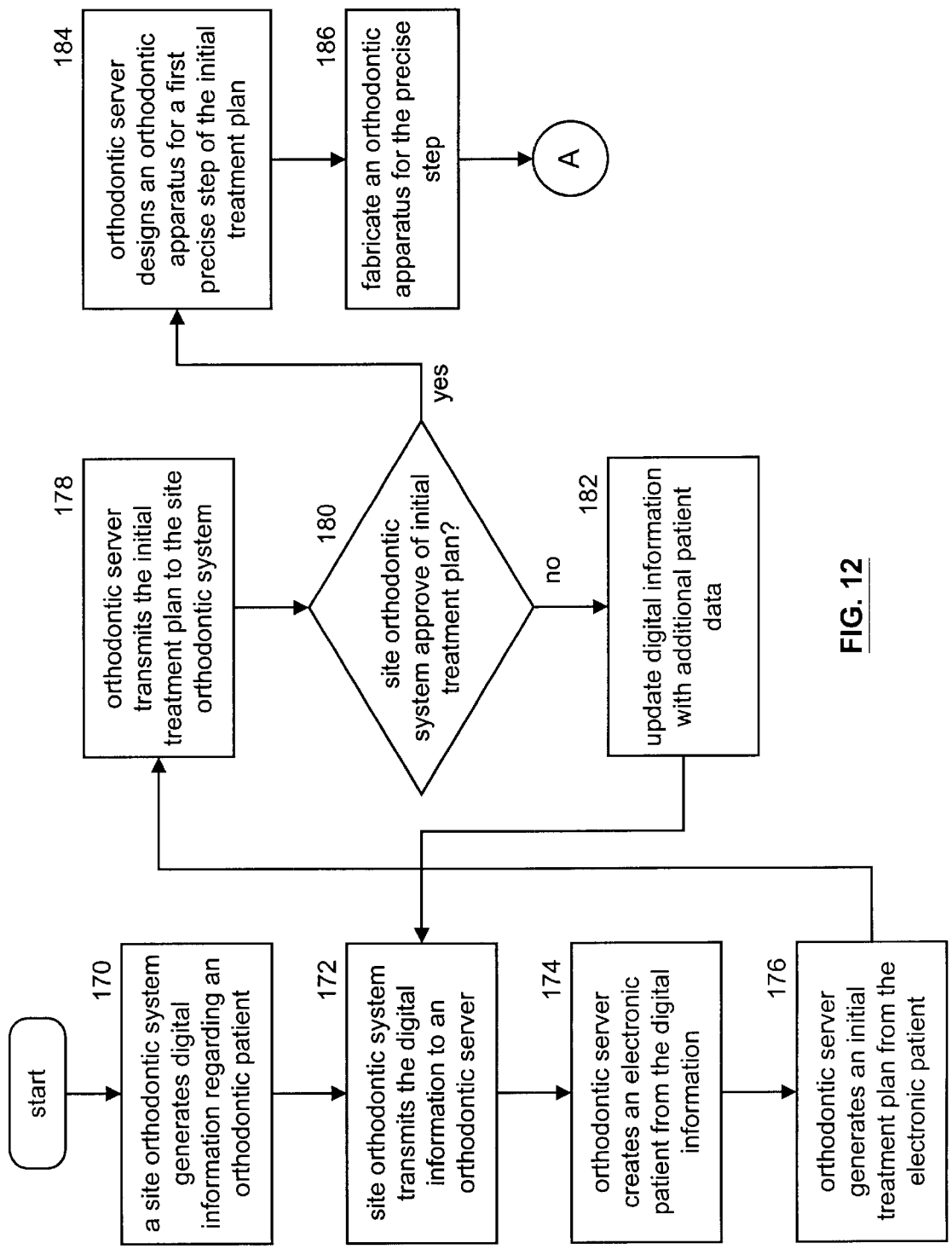
Figure 13:
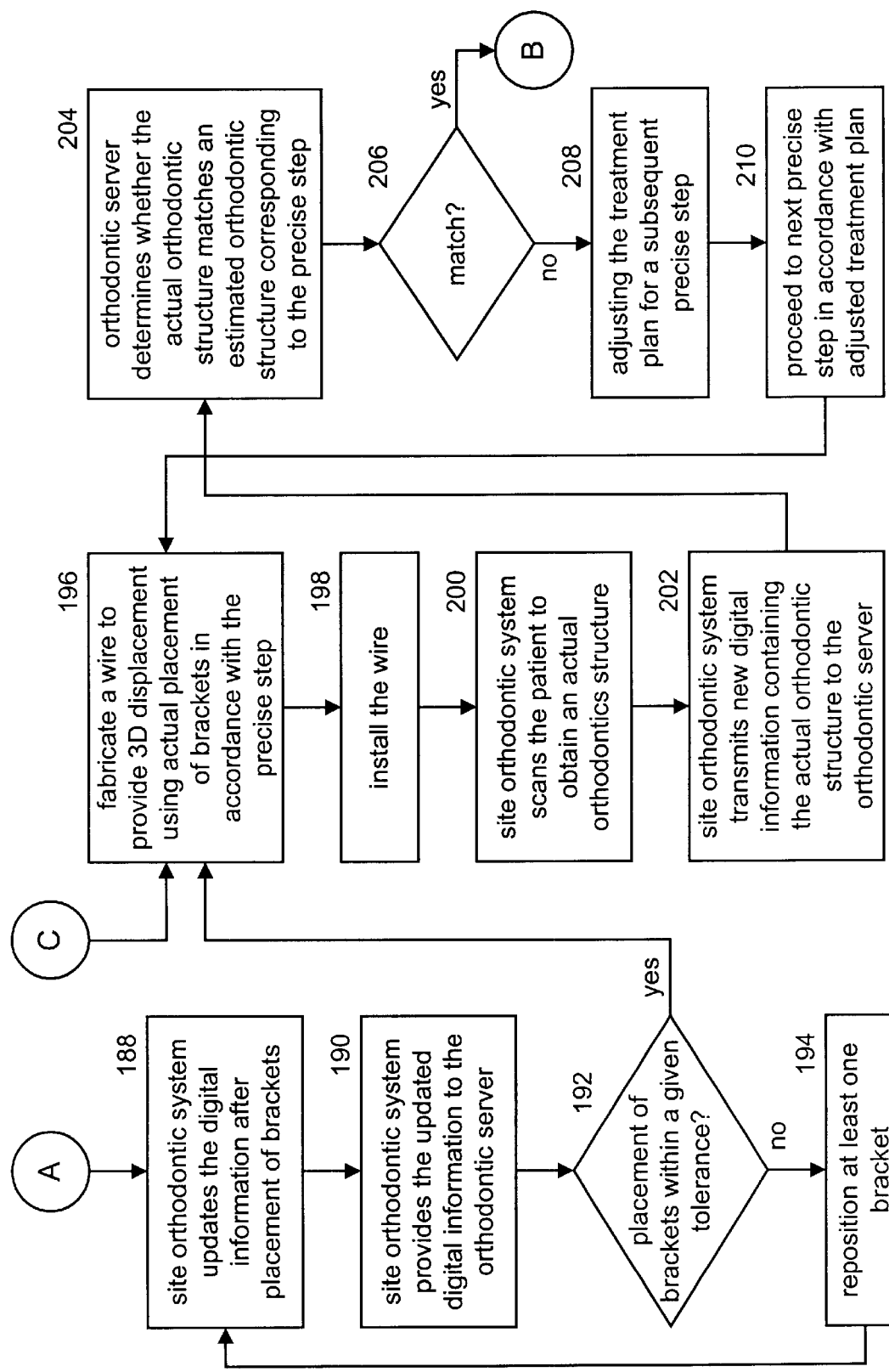

FIGS. 12 through 14 illustrate a logic diagram performed by the orthodontic system 10 and 50. The process begins at step 170 where a site orthodontic system generates digital information regarding an orthodontic patient. The digital information includes, but is not limited to, a three-dimensional image of the orthodontic patient's orthodontic structure, a two-dimensional image of the orthodontic' patient's orthodontic structure (e.g., x-rays and pictures) and patient data. Note that the three-dimensional image may be obtained by scanning the patient's mouth to obtain video data thereof and converting the video data into a three-dimensional image. The process then proceeds to step 172 where the orthodontic site transmits the digital information to an orthodontic server. The digital information may be transmitted via an Internet connection, a local area network connection, a wide-area network connection, a direct connection, a direct connection, and/or a modem connection. The process then proceeds to step 174 where the orthodontic server creates an electronic patient record from the digital information and is updated as further information is obtained. The electronic patient record includes, but is not limited to, clinical examination interpretations, radiology examination and measurements, automatic and/or manual cephalometric analysis, orthodontic history, mechanics plan, treatment objective, credit history, chronological data, task delegation, risk analysis, ordering information for orthodontic apparatus, electronic cephalometric tracings, integrated three-dimensional images and radiology and photograph images into an electronic composite, electronic articulation models, measurements and analysis of the electronic models, data quality assurance checks, and/or supplemental data.

The process then proceeds to step 176 where the orthodontic server generates an initial treatment plan for the electronic patient. To generate the initial treatment plan, the orthodontic server determines whether a multi-disciplinary treatment is involved. In other words, does the patient require additional medical treatment beyond orthodontic care. If so, a physician is consulted to obtain additional medical treatment information.

The orthodontic server also determines whether interdisciplinary treatment is needed. As such, the orthodontic server determines whether other dental work is required beyond orthodontic treatment. For example, does the patient require tooth extraction. If so, the interdisciplinary treatment is added to the initial treatment plan. In addition, special treatment may be further required such as unique brackets, wiring, etc. If special treatment is required, orthodontic parameters are retrieved from a database wherein the orthodontic parameters are identified by cross matching at least some of the characteristics of the electronic patient record with orthodontic parameters of other electronic patient records. A first pass treatment plan is then generated based on the orthodontic parameters in the electronic patient record. The special treatment information is then integrated with the first pass treatment plan to produce the initial treatment plan. If special treatment is not required, the first pass plan is used as the initial treatment plan.

The process then proceeds to step 178 where the orthodontic server transmits the initial treatment plan to the site orthodontic system. The process then proceeds to step 180 where a determination is made as to whether the site orthodontic system approved of the initial plan via inputs from a practitioner. If not, the process proceeds to step 182 where digital information regarding the patient is updated with additional patient data. The process then reverts to step 172.

If, however, the site orthodontic system approves of the initial treatment plan, the process proceeds to step 184. At step 184 the orthodontic server designs an orthodontic apparatus for a first precise step of the initial treatment plan. Note that the initial design may be enhanced by the use of a remote diagnostic computer such that additional experts may be consulted to generate the treatment and/or orthodontic apparatus. The process then proceeds to step 186 where the orthodontic apparatus is fabricated for the first precise step. If indirect bonding is to be used, the orthodontic apparatus includes brackets, an active wire, a passive wire, specialty appliances and indirect bonding tray. If direct bonding is to be used, the orthodontic apparatus includes brackets, a first active wire, a passive wire, and specialty appliances. Note that the active wire includes the three-dimensional bends that apply the three-dimensional displacement of the tooth and a passive wire provides zero forces upon a given tooth. Further note that the wire may include an active portion and a passive portion.

The process then proceeds to step 188 of FIG. 13. At step 188, the site orthodontic system updates the digital information after placement of the brackets. The process then proceeds to step 90 where the site orthodontic system provides the updated digital information to the orthodontic server. The process then proceeds to step 192 where a determination is made as to whether placement of the brackets is within a given tolerance. If not, the process proceeds to step 194 where at least one bracket is repositioned. Having repositioned the brackets, the process reverts to step 188. Note that the determination of whether the brackets are within a given tolerance may be done in real time such that the repositioning of the brackets has minimal impact on the patient's care and/or time of treatment.

If the placement of the brackets is within a given tolerance with respect to an error vector, the process proceeds to step 196. At step 196, a wire is fabricated to provide three-dimensional displacement using the actual placement of the brackets in accordance with the first precise step. Note that the orthodontic apparatus includes brackets, a wire, bands, auxiliary appliances, headgear, rubber band placement and/or a retaining structure. The process then proceeds to step 198 where the wire is installed into the patient's mouth. The process proceeds to step 200 where the site orthodontic system scans the patient's mouth to obtain an actual orthodontic structure. The process then proceeds to step 202 where the site orthodontic system transmits the new digital information containing the actual orthodontic structure to the orthodontic server.

The process then proceeds to step 204 where the orthodontic server determines whether the actual orthodontic structure matches an estimated orthodontic structure corresponding to the precise step. The process then proceeds to step 206 where a branch occurs depending on whether a match occurs within step 204. If a match does not occur, the process proceeds to step 208 where the treatment plan is adjusted for subsequent precise steps. As such, the treatment plan is revised to correct for the non-compliant tooth movement. The process then proceeds to step 210 where the treatment of the patient proceeds to the next precise step in accordance with the adjusted treatment plan. Having done this, the process reverts to step 196. Note that, even if a matched occurred at step 206, the practitioner may choose to make an adjustment to expedite treatment. As such, step 208 would be used to achieve the expedited treatment.

If a match occurs between the actual orthodontic structure and the estimated orthodontic structure, the process proceeds to step 212 of FIG. 14. At step 212 a determination is made as to whether the treatment is complete. If so, the process proceeds to step 216 where the orthodontic server designs a retaining device using the electronic patient record which has been updated throughout the treatment. Note that the orthodontic server may design the retaining device at or near the completion of treatment. If the treatment is not complete, the process proceeds to step 214 where the treatment of the patient proceeds to the next step in accordance with the initial treatment plan. Upon proceeding to the next step, the process reverts to step 196 of FIG. 13.

FIG. 15 illustrates a logic diagram of a method for the site orthodontic system to support the treatment of an orthodontic patient. The process begins at step 220 where digital information regarding an orthodontic patient is generated. The digital information includes a three-dimensional image of the patient's orthodontic structure, a two-dimensional image of the orthodontic patient's orthodontic structure and patient data. The process then proceeds to step 222 where the digital information is transmitted to an orthodontic server. The process then proceeds to step 224 where a digital version of the treatment plan is received. Upon receiving the treatment plan, the site orthodontic system may transmit a confirmation acknowledgment to the orthodontic server.

The process then proceeds to step 226 where the digital information is updated after the placement of the brackets. If a bracket were misplaced, the bracket would be repositioned and the digital information would be updated. The process then proceeds to step 228 where the updated digital information is transmitted to the orthodontic server. The process then proceeds to step 230 where digital information is generated for each application of an orthodontic structure in accordance with one of the precise steps. As the digital information is generated, it is transmitted to the orthodontic server. This continues until the treatment is complete. In addition, updates of the patient treatment may be provided to the patient, via a soft copy using email or a hard copy, to a care provider, and/or to any other practitioner associated with the treatment of the patient. Such updates may correspond to the precise steps of the treatment plan, scheduled visits of the patient, and/or any other desired triggering event.

Figure 16:
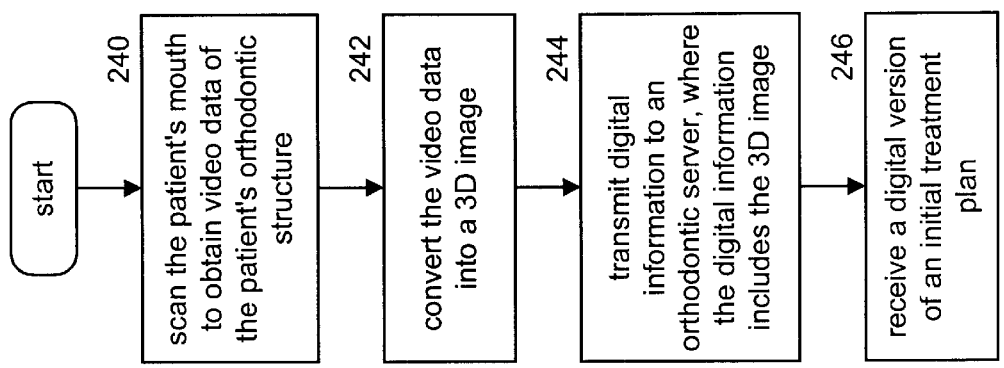
FIG. 16 illustrates a logic diagram of an alternate method for monitoring a patient's progress during treatment in accordance with the present invention.

FIG. 16 illustrates a logic diagram of an alternate method for the site orthodontic system to assist in the treatment of an orthodontic patient. The process begins at step 240 where the patient's mouth is scanned to obtain video data of the orthodontic patient structure. The process then proceeds to step 242 where the video data is converted into a three-dimensional image. The process then proceeds to step 244 where the digital information is transmitted to an orthodontic server where the digital information includes a three-dimensional image. The process then proceeds to step 246 where a digital version of the initial treatment is received.

Using an iterative method in accordance with the present invention is advantageous over prior methods that were ultimately based upon a single two-dimensional analysis. By using a three-dimensional model in accordance with a specific embodiment of the present invention in conjunction with an iterative process, any factor that effects tooth movement (i.e. brackets, wires, adhesion, physiological changes) can be simulated to determine appropriate treatment changes. Such compensation in treatment is not possible using prior methods which were based upon assumptions from a single model that the tooth movement would progress in a known manner. Therefore, the prior art methods would specify and a single static treatment based upon this assumption. If any unwanted tooth movement occurred during treatment, the specified treatment would no longer be valid, requiring changes to be made based upon a practitioner's expertise. The present system provides a dynamic system that through the use of periodic feedback, i.e. periodic three-dimensional scanning, can be monitored and adjusted as needed by the system in an efficient manner. As such, unexpected tooth movement, such as occurs when a patient does not cooperate, or through biological changes, can be readily controlled.

The preceding discussion has presented a method and apparatus for treating an orthodontic patient. By utilizing a closed-loop system in accordance with the present invention, each step of the treatment may be monitored and correspondingly adjusted, if needed, thereby providing a more cost efficient and effective orthodontic treatment. In addition, by utilizing wires to provide three-dimensional displacement of a tooth, expensive custom brackets are not required thereby further reducing the cost of, and improving the accuracy of, orthodontic treatment. Alternatively, the system may be used in an open loop manner to provide one-time diagnostic information, bracket placement verification, and/or generation of the orthodontic apparatus without monitoring. As one of average skill in the art would appreciate, other embodiments may be derived from the teaching of the present invention without deviating from the scope of the claims.

What is claimed is:

1. A method for treating an orthodontic patient, the method comprises the steps of:
   a) generating digital information regarding the orthodontic patient by a site orthodontic system;
   b) transmitting the digital information from the site orthodontic system to an orthodontic server;
   c) creating, by the orthodontic server, an electronic patient record from the digital information;
   d) generating, by the orthodontic server, an initial treatment plan from the electronic patient record, wherein the initial treatment plan includes one or more tooth movement steps to obtain a desired orthodontic structure;
   e) transmitting, by the orthodontic server, a digital version of the initial treatment plan to site orthodontic system;
   f) designing, by the orthodontic server, an orthodontic apparatus for one of the steps upon receipt of treatment plan confirmation from the site orthodontic system;
   g) fabricating the orthodontic apparatus;
   h) scanning the patient's orthodontic structure with a scanner after the orthodontic apparatus has been installed on the patient and time has elapsed to result in movement of the patient's teeth; and
   i) comparing the patient's actual orthodontic structure with an estimated orthodontic structure based on the treatment plan and responsively adjusting the treatment plan in the event that the actual orthodontic structure is not as predicted.

2. The method of claim 1 further comprising the steps of:
   updating the digital information by the site orthodontic system after placement of a portion of the orthodontic apparatus, said updating including said step (h) of scanning;
   providing, by the site orthodontic system, the updated digital information to the orthodontic server;
   determining, by the orthodontic server, whether the placement of the portion of the orthodontic apparatus has been placed within a given tolerance; and
   fabricating a second portion of the orthodontic apparatus to provide passive or active three-dimensional displacement in relation to the placement of the portion of the orthodontic structure in accordance with the one of the steps when the placement of the portion of the orthodontic apparatus has been placed within the given tolerance.

3. The method of claim 2 further comprising the step of:
   further updating the digital information after replacement of the brackets when the placement of at least one of the brackets exceeds the given tolerance.

4. The method of claim 1 further comprising the steps of:
   determining whether an actual orthodontics structure of the patient for the orthodontics apparatus substantially matches an estimated orthodontics structure of the patient, wherein the estimated orthodontics structure is derived in accordance with the initial treatment plan, or a revised treatment plan, and the precise step; and
   when the actual orthodontics structure does not substantially match the estimated orthodontics structure, adjusting the initial treatment plan, or the revised treatment plan, for a subsequent precise step to obtain the desired orthodontics structure.

5. The method of claim 4 further comprises when the actual orthodontics structure substantially matches the estimated orthodontics structure, generating a next corresponding orthodontics structure for a next precise step of the initial treatment plan.

6. The method of claim 4, wherein the orthodontics apparatus further comprises at least one of: brackets, bands, a wire, head gear, rubber band placement, auxiliary appliances, and a retaining structure.

7. The method of claim 1, wherein step (a) further comprises generating the digital information to include a three-dimensional image of the orthodontic patient's orthodontic structure, a two dimensional image of the orthodontic patient's orthodontic structure, and patient data.

8. The method of claim 7 further comprising the steps of:

scanning the orthodontic patient's mouth to obtain data of the patient's orthodontic structure; and converting the data into the three-dimensional image.

9. The method of claim 1, wherein step (b) further comprises transmitting the digital information to the orthodontic server via at least one of: an internet connection, a local area network connection, a wide area network connection, a direct connection, and a modem connection.

10. The method of claim 1, wherein step (d) further comprises:

obtaining supplemental treatment information when special treatment is required;

obtaining orthodontic parameters for the orthodontic patient from a database of orthodontic parameters, wherein the orthodontic parameters are identified by cross-matching at least some characteristics of the electronic patient record with orthodontic parameters of other electronic patient records;

generating a first pass treatment plan based on the orthodontic parameters and the electronic patient record; and integrating the special treatment information with the first pass treatment plan to produce the initial treatment plan.

11. The method of claim 1, wherein step (d) further comprises:

obtaining orthodontic parameters for the orthodontic patient from a database of orthodontic parameters, wherein the orthodontic parameters are identified by cross-matching at least some characteristics of the electronic patient record with orthodontic parameters of other electronic patient records; and generating the initial treatment plan based on the orthodontic parameters and the electronic patient record.

12. The method of claim 1 further comprises, for each application of a corresponding apparatus of the initial treatment plan, generating a three-dimensional image of the orthodontic patient's current orthodontic structure; and providing the three-dimensional image to the orthodontic server.

13. The method of claim 1 further comprises designing, by the orthodontic server, a retaining device for the orthodontic patient at or near completion of the initial treatment plan.

14. The method of claim 1, wherein step (f) further comprises receiving, by the orthodontic server, design inputs from a diagnostic computer.

15. A system for treating an orthodontic patient, the system comprises:

a scanner operable to obtain data of an orthodontic structure of a patient;

a site orthodontic system operably coupled to the scanner, wherein the site orthodontic system receives the data and produces therefrom a three-dimensional image of the orthodontic structure, wherein the site orthodontic system obtains a two-dimensional image of the orthodontic structure, and patient data, and wherein the three-dimensional image, the two-dimensional image, and the patient data constitutes patient orthodontic information;

an orthodontic server operably coupled to the site orthodontic system to receive the patient orthodontic information and to produce therefrom an electronic patient record, wherein the orthodontic server generates an initial treatment plan for the patient based on the electronic patient record and orthodontic parameters, wherein the initial treatment plan includes one or more steps to obtain a desired orthodontic structure, and wherein the orthodontic server designs an orthodontic apparatus in accordance with one of the steps; and a wire bending device operably coupled to produce a wire of the orthodontic apparatus based on the design of the orthodontic apparatus, wherein the wire provides three-dimensional displacement of at least one tooth of the orthodontic structure;

wherein the scanner is adaptable to scan in vivo the patient's orthodontic structure after the orthodontic apparatus has been installed on the patient and time has elapsed to result in movement of the patient's teeth; and wherein said orthodontic server comprises software for comparing the patient's actual orthodontic structure with an estimated orthodontic structure based on the treatment plan and responsively adjusting the treatment plan in the event that the actual orthodontic structure is not as predicted.

16. The system of claim 15 wherein the orthodontic server further comprises a software module for:

determining whether actual orthodontics structure for the orthodontics apparatus substantially matches an estimated orthodontics structure, wherein the estimated orthodontics structure is derived in accordance with the initial treatment plan and the precise step; and when the actual orthodontics structure does not substantially match the estimated orthodontics structure, adjusting the initial treatment plan for subsequent precise steps to obtain the desired orthodontics structure.

17. The system of claim 15, wherein the orthodontics structure further comprises at least one of: brackets, a wire, head gear, rubber band placement, and a retaining structure.

18. The system of claim 15, further comprises:

a database of orthodontic parameters operably coupled to the orthodontic server, wherein the orthodontic server:

obtains special treatment information when special treatment is required;

obtains orthodontic parameters for the orthodontic patient from a database of orthodontic parameters, wherein the orthodontic parameters are identified by cross-matching at least some characteristics of the electronic patient record with orthodontic parameters of other electronic patient records;

generates a first pass treatment plan based on the orthodontic parameters and the electronic patient record; and integrates the special treatment information with the first pass treatment plan to produce the initial treatment plan.

19. The system of claim 15 further comprises:

a database of orthodontic parameters operably coupled to the orthodontic server, wherein the orthodontic server:

obtains orthodontic parameters for the orthodontic patient from a database of orthodontic parameters, wherein the orthodontic parameters are identified by cross-matching at least some characteristics of the electronic patient record with orthodontic parameters of other electronic patient records; and generates the initial treatment plan based on the orthodontic parameters and the electronic patient record.

20. The system of claim 15 further comprises a diagnostic computer that provides design inputs to the orthodontic server.

* * * * *